US012797303B2

(12) United States Patent
O'Grady et al.

(10) Patent No.: US 12,797,303 B2
(45) Date of Patent: Nov. 17, 2026

(54) FEEDING CATHETER

(71) Applicant: THE INSIDES COMPANY LIMITED, Auckland (NZ)

(72) Inventors: Gregory Brian O'Grady, Auckland (NZ); John Bilkey Davidson, Auckland (NZ); Kaitlyn Chu, Auckland (NZ); Robert Bruce Davidson, Auckland (NZ)

(73) Assignee: THE INSIDES COMPANY LIMITED, Auckland (NZ)

( * ) Notice: Subject to any disclaimer, the term of this patent is extended or adjusted under 35 U.S.C. 154(b) by 439 days.

(21) Appl. No.: 18/556,371

(22) PCT Filed: Apr. 21, 2022

(86) PCT No.: PCT/IB2022/053715
§ 371 (c)(1),
(2) Date: Oct. 20, 2023

(87) PCT Pub. No.: WO2022/224175
PCT Pub. Date: Oct. 27, 2022

(65) Prior Publication Data

US 2024/0189193 A1 Jun. 13, 2024

(30) Foreign Application Priority Data

Apr. 22, 2021 (NZ) ........................................ 775347

(51) Int. Cl.

| | |
|---|---|
| ***A61J 15/00*** | (2006.01) |
| ***A61M 25/00*** | (2006.01) |
| ***A61M 25/04*** | (2006.01) |
| *A61J 9/00* | (2006.01) |
| *A61M 39/02* | (2006.01) |

(52) U.S. Cl.
CPC ....... *A61J 15/0015* (2013.01); *A61J 15/0034* (2013.01); *A61J 15/0038* (2013.01);
(Continued)

(58) Field of Classification Search
CPC ................ A61J 15/0015; A61J 15/0038; A61J 15/0061; A61J 15/0065; A61J 15/0069;
(Continued)

(56) References Cited

U.S. PATENT DOCUMENTS 4,642,092 A * 2/1987 Moss ...................... A61M 1/85
604/102.03
5,248,302 A * 9/1993 Patrick ................ A61J 15/0015
604/105
(Continued)

FOREIGN PATENT DOCUMENTS

DE 3432937 A * 5/1985 ............ A61M 25/02
EP 0648512 A1 * 4/1995 .......... A61J 15/0061
(Continued)

*Primary Examiner* — Wesley G Harris
(74) *Attorney, Agent, or Firm* — Niels Haun; Dann, Dorfman, Herrell & Skillman, P.C.

(57) ABSTRACT

An improved feeding catheter is provided for feeding/recycling chyme to a distal stoma. The improved catheter includes a hollow tube having an end for insertion into stoma, and a second end adapted to be connected to a fluid source. The first end includes a retention feature comprising a plurality of ribs extending outwardly and longitudinally away from the tube and terminating at a nose junction. Web walls extend between at least one pair of adjacent ribs and the ribs further define a side facing opening configured for fluid to exit into the gastrointestinal tract. Further the retention feature can be moved between a relaxed condition and a stretched condition for insertion through the distal opening, wherein the maximum width of the retention feature in the stretched condition is less than the maximum width of the retention feature in the relaxed condition.

20 Claims, 9 Drawing Sheets

(52) U.S. Cl.
CPC ....... *A61J 15/0046* (2013.01); *A61J 15/0061* (2013.01); *A61J 15/0069* (2013.01); *A61J 15/0076* (2015.05); *A61M 25/0074* (2013.01); *A61M 25/04* (2013.01); *A61J 9/005* (2013.01); *A61M 2039/0255* (2013.01)

(58) Field of Classification Search
CPC ................ A61J 15/0023; A61J 15/0057; A61J 15/0034; A61J 15/0092; A61J 15/0076; A61J 15/0026; A61J 15/0046; A61J 9/005; A61M 25/04; A61M 2025/0233; A61M 2039/0255; A61M 25/0074; A61B 2017/3484
See application file for complete search history.

(56) References Cited

U.S. PATENT DOCUMENTS 5,267,969 A * 12/1993 Hirsch ................ A61J 15/0061 604/174
5,273,529 A * 12/1993 Idowu ................. A61J 15/0065 604/537
5,749,826 A * 5/1998 Faulkner ............... A61F 2/0009 604/537
2008/0058730 A1* 3/2008 Melsheimer ....... A61B 17/3417 604/177
2010/0057013 A1* 3/2010 Harada ................. A61M 25/04 604/175
2010/0185155 A1* 7/2010 McMichael ......... A61J 15/0038 604/175
2012/0238959 A1* 9/2012 Thorne ................. A61M 25/02 604/177
2020/0390590 A1* 12/2020 O'Grady ................. A61M 1/00

FOREIGN PATENT DOCUMENTS

WO WO-9427656 A1 * 12/1994 .......... A61J 15/0065
WO WO-2006111416 A1 * 10/2006 ............ A61M 25/04
WO WO-2011018682 A2 * 2/2011 .......... A61J 15/0057
WO WO-2011069505 A1 * 6/2011 ........ A61M 25/0015
WO WO-2019073365 A1 * 4/2019 ............. A61F 5/441

* cited by examiner

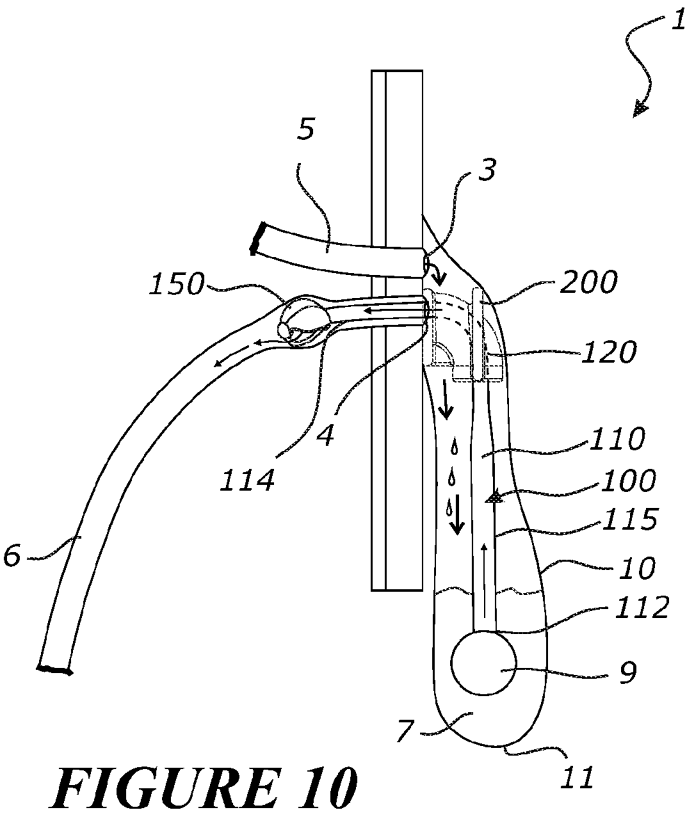
FIGURE 10
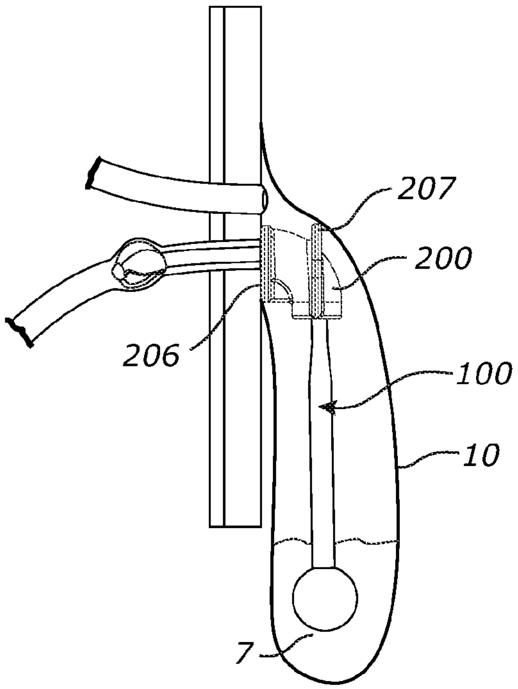
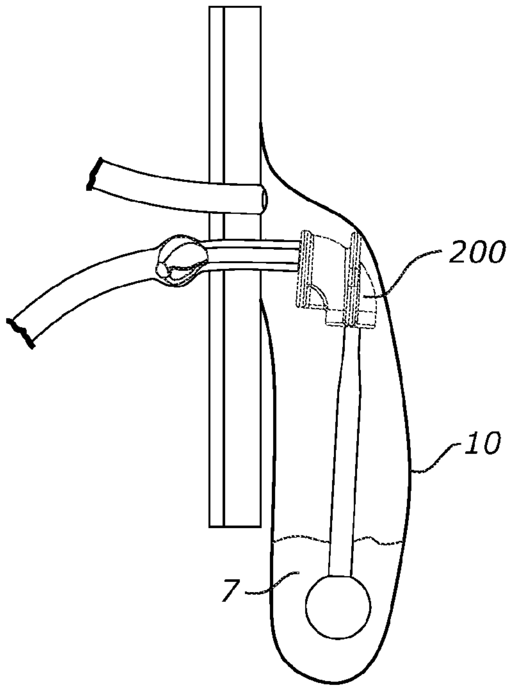
FIGURE 11
FIGURE 12

FEEDING CATHETER

FIELD OF THE INVENTION

The present invention relates to an improved feeding catheter. More particularly, the feeding catheter is suitable for use with a stoma device. More particularly still, it relates to an improved feeding catheter for introducing fluid contents to a distal portion of the gastrointestinal tract.

BACKGROUND OF THE INVENTION

Colorectal cancer is a cancer which develops from the colon or rectum and is currently the third most prevalent cancer worldwide. Patients with colorectal cancer often require the use of a stoma bag after surgery. Ileostomies remain a cornerstone of colorectal cancer management, particularly for rectal cancer management. Ileostomy involves dividing the ileum (the distal small bowel) and bringing one or both ends onto the skin of a patient so that digestive contents can flow into a stoma bag. Traditionally, the digestive contents bypass the colon and are collected in the stoma bag and then emptied manually, thereby bypassing the colon that normally reabsorbs fluid, electrolytes, microbiome and nutrients.

A loop ileostomy is a common type of ileostomy which is intended to temporarily divert digestive contents, while the gastrointestinal tract distal to the ileum heals after colorectal surgery. It is usually intended that the loop ileostomy will be reversed by re-connecting the divided ends of the bowel back together, once healing has occurred. A radiological test is usually performed before the reversal surgery, to confirm that healing has occurred and that the bowel is not leaking. Usually a patient requires at least 1-2 weeks for their gastrointestinal tract distal to the ileum to heal sufficiently to perform a radiological leak test and consider reversal surgery.

After a leak test, some patients may have an “early reversal” of their ileostomy, performed within 1-2 weeks after surgery. However, it is more usual for ileostomy reversal surgery to occur around 6-12 weeks after surgery. It is generally not considered to be safe to perform the reversal surgery between 2-6 weeks after surgery, because of the presence of internal adhesions that increase surgical risk. If a patient is having chemotherapy, they may need to retain an ileostomy for many months until the chemotherapy is finished, before surgery can be safely performed.

As digestive contents are evacuated from the patient’s body, patients may suffer from fluid, electrolyte and nutrient losses as ileostomy bypasses the colon which resorbs water, electrolytes and certain nutrients. As a result, patients may experience dehydration and subsequent renal injury, and may need to be readmitted to hospital for management with intravenous fluid replacement, known as parenteral nutrition. Parenteral nutrition is expensive, and has risks of line infections and liver complications. Further, patients may also require additional medications (to slow intestine transit), antibiotics, faecal transplants or poorly tolerated oral rehydration solutions—all requiring additional hospital resources Some patients have “high output” ileostomies, being at increased risk of dehydration and renal injury, and may therefore need to be additionally managed with medications that slow gut transit, and with oral rehydration solutions that may be poorly tolerated. Stoma patients often use a lot of hospital resources due to the additional management required, and the related readmissions due to stoma-related dehydration.

Ileostomy patients having chemotherapy, may also suffer excessive stoma output during chemotherapy, which leads to dose reductions and suboptimal therapy. Leaving the colon without any internal nutrients for an extended duration may also increase the risk of “anterior resection syndrome”, which is poor bowel function after rectal cancer surgery. Anterior resection syndrome is associated with a poorer quality of life in colorectal cancer survivors.

When an ileostomy is reversed, patients may experience ileus (slow recovery of gut function), partly due to the poor condition of the gut distal to the ileostomy due to the lack of nutrition. A loop ileostomy also depletes the bacterial microbiome that normally occupies the colon, which contributes to colonic health, and as a result, patients undergoing reversal surgery may experience *Clostridium difficile* infections. *Clostridium difficile* infections prolong hospital stay, can cause serious illness, and may require additional treatments such as antibiotics, surgery or fecal transplants.

Another group of patients who may require a stoma bag are patients with enterocutaneous fistulas, which is an abnormal connection between the gut and the skin. An enterocutaneous fistula may arise as a complication of surgery, or due to a traumatic injury, or because of another disease process such as inflammatory bowel disease. Some neonates may get enterocutaneous fistulas or stomas because of a disease called necrotising enterocolitis, where a segment of gut becomes necrotic.

A type of ‘stoma’ bag is usually placed over the enterocutaneous fistula to catch the digestive contents. Patients with fistulas often experience poor nutrition and may become dependent on supplementary feeding such as parenteral nutrition, which is given through a vein. Parenteral nutrition is usually an expensive and risky treatment due to the possibilities of line infections and liver damage.

A nutrient recycling device can be used to collect digestive contents from a proximal opening of the ileum into a stoma bag and recycle/transfer the contents from the stoma bag to a distal opening of the ileum. For example, the applicant’s nutrient recycling device as disclosed in PCT/IB2018/057792 can recycle digestive contents from a proximal opening, to a distal opening of the ileum. These devices can reduce or eliminate dehydration and renal impairment due to traditional ileostomies. The nutrient recycling device may also reduce the burden of waste content management associated with stoma bags.

To introduce the digestive contents collected in the stoma bag into the distal opening of the ileum, a catheter may be used. However, traditional catheters are generally not well suited to be used to feed digestive contents from a stoma bag to the distal opening of the ileum. For example, other traditional types of catheters include balloon catheters, Malecot catheters, and Pezzer catheters. Balloon catheters retain themselves by expansion of a balloon. The problem with balloon catheters is that they can over expand that may cause damage or rupture the intestine. Another disadvantage of balloon catheters is that they cannot be cut in length as the inflation channel would also be cut and the balloon deflated.

Malecot and Pezzer catheters have more openings and sharper edges introducing the problem that they may cause granulation that encourages ingrowth of tissue into the tube that may require surgery to be removed.

An improved feeding catheter customised to feed contents from a bag, such as a flexible stoma bag positioned over a stoma or fistula, to a distal opening of the ileum may be desirable, and is provided herein.

In this specification, where reference has been made to external sources of information, including patent specifications and other documents, this is generally for the purpose of providing a context for discussing the features of the present invention. Unless stated otherwise, reference to such sources of information is not to be construed, in any jurisdiction, as an admission that such sources of information are prior art or form part of the common general knowledge in the art.

For the purpose of this specification, where method steps are described in sequence, the sequence does not necessarily mean that the steps are to be chronologically ordered in that sequence, unless there is no other logical manner of interpreting the sequence.

It is an object of the present invention to provide an improved feeding catheter which overcomes or at least partially ameliorates some of the abovementioned disadvantages or which at least provides the public with a useful choice.

BRIEF DESCRIPTION OF THE INVENTION

According to a first aspect the invention broadly comprises a feeding catheter adapted to transfer fluid into an opening of a gastrointestinal tract, the feeding catheter comprising:

- a hollow tube having:
  - a first end adapted to be inserted into a distal portion of the gastrointestinal tract through a distal opening;
  - a second end adapted to be connected to a fluid source; and
  - a tube lumen between the first end and the second end of the hollow tube defining a fluid pathway;
- a retention feature adapted to retain at least a portion of the feeding catheter in the distal portion of the gastrointestinal tract, the retention feature located at or towards the first end of the hollow tube and comprises:
  - an insertion end and a trailing end, the trailing end located at or towards the first end of the hollow tube;
  - a plurality of ribs extending outwardly and longitudinally away from the hollow tube and terminating at a nose junction;
  - a web wall extending between at least one pair of adjacent ribs;
  - a side facing opening located between at least one pair of adjacent ribs configured for fluid to exit into the gastrointestinal tract; and
- wherein the retention feature comprises a relaxed condition and a stretched condition for insertion through the distal opening; and
- wherein the maximum width of the retention feature in the stretched condition is less than the maximum width of the retention feature in the relaxed condition.

According to another aspect the retention feature forms a partially open bulbous shape in the relaxed condition.

According to another aspect the pair of adjacent ribs forming the side facing exit lacks a web wall between the ribs.

According to another aspect the side exit forms a generally circular opening.

According to another aspect the retention feature comprises a single facing side exit.

According to another aspect the single side facing exit is located between a single pair of adjacent ribs.

According to another aspect the adjacent ribs forming the side exit are spaced apart a greater distance than the adjacent ribs joined by web walls.

According to another aspect the ribs forming the side exit have an angular orientation less than 180° apart.

According to another aspect the ribs forming the side exit have an angular orientation of approximately 140° apart.

According to another aspect the side facing exit provides an opening for a majority or all of the fluid to exit into the gastrointestinal tract from the feeding catheter.

According to another aspect the web wall is a flexible membrane.

According to another aspect the web wall has a wall thickness less than a wall thickness of the plurality of ribs.

According to another aspect the web wall has a wall thickness less than 20% the wall thickness of the ribs.

According to another aspect the web wall has a wall thickness of approximately 10% to 20% of the wall thickness of the ribs.

According to another aspect the web wall is configured to collapse generally inwardly in the stretched condition.

According to another aspect the web wall collapses between the ribs in the stretched condition.

According to another aspect the web wall comprises a score-line to assist the web wall to collapse when moving to the stretched condition.

According to another aspect the score-line is a longitudinal indent along the web wall.

According to another aspect the tube lumen is configured to receive an introducer.

According to another aspect the introducer is configured to engage with an internal surface of the nose junction to force the retention member from the relaxed condition to the stretched condition.

According to another aspect the retention feature further comprises a pocket on the inner surface of the nose junction to receive a tip of the introducer.

According to another aspect the nose junction is diametrically opposed the first end of the hollow tube.

According to another aspect the feeding catheter further comprises an aperture on the hollow tube towards the first end of the tube to provide a suction break.

According to another aspect the retention feature comprises three to five ribs.

According to another aspect the retention feature comprises three ribs.

According to another aspect the hollow tube comprises:

- a neck portion located towards the first end; and
- an extended diameter portion located towards the second end, and
- wherein the extended diameter portion has a tube diameter greater than the neck portion.

According to another aspect the extended diameter portion comprises a length at least 40% of the feeding catheter length, and is adapted to be cut to length as desired.

According to another aspect wherein the extended diameter portion comprises a length at least 25% of the feeding catheter length, and is adapted to be cut to length as desired.

According to another aspect the extended diameter portion comprises an external diameter approximately between 10 mm and 20 mm.

According to another aspect the extended diameter portion comprises an external diameter approximately between 10 mm and 15 mm.

According to another aspect the neck portion comprises an external diameter approximately between 4 mm and 12 mm.

According to another aspect the neck portion comprises an external diameter approximately between 8 mm and 10 mm.

According to another aspect the feeding catheter is made of a resilient material.

According to another aspect the resilient material is medical grade silicone.

According to another aspect the feeding catheter is an integrated component.

According to another aspect the first end of the hollow tube is adapted to be inserted into an ileum.

According to another aspect the fluid source is provided by a pump adapted to drive the fluid into the hollow tube.

According to another aspect the feeding catheter is adapted for use with a device recycling fluid digestive contents from a proximal opening of a gastrointestinal tract to the distal opening of the gastrointestinal tract.

According to another aspect the opening(s) of the gastrointestinal tract are stomas or fistulas.

According to another aspect the invention broadly comprises an elbow guide comprising:

- an at least semi-rigid elbow guide for receiving and guiding the feeding catheter in a flexible bag, the at least semi-rigid elbow guide comprising:
  - a guide body having a first end and a second end, and a guiding passageway extending between the first end and second end for the feeding catheter to pass through, the guide passageway having a bend for maintaining the catheter in a bent position and the guiding passageway having a first passage opening and a second passage opening; and
  - a flange at the first end of the guide body to engage with an exterior surface of the patient's body adapted to maintain the position of the feeding catheter; and
- wherein the first passage opening is located towards an edge of the flange such that there is a substantial engaging surface area located away from the edge to engage with the exterior surface of the patient's body; and
- wherein the at least semi-rigid elbow guide is positioned over the feeding catheter to maintain the catheter in a bent position.

According to another aspect the invention broadly comprises an assembly including a feeding catheter as described in any of the previous clauses and the elbow guide of the previous clause.

According to another aspect the at least semi-rigid elbow guide is slidably moveable relative to the feeding catheter to adjust the catheter bent position.

According to another aspect the at least semi-rigid elbow guide comprises an elbow bend adapted to guide the feeding catheter downwards such that the second end is located towards a bottom region of the flexible bag.

According to another aspect the at least semi-rigid elbow guide is positioned to set the depth of insertion of the feeding catheter into the patient.

According to another aspect the flange provides a substantially flat surface adapted to engage an inner surface of the flexible bag.

According to another aspect the elbow guide assembly further comprising a secondary flange spaced from the flange, the secondary flange comprises a diameter or width greater than the flange.

According to another aspect the guide body comprises a plurality of cantilevered fingers generally encompassing the guiding passageway and configured to resiliently grip a feeding catheter.

According to another aspect there are at least 3 cantilevered fingers arranged to alternately interleave one another.

According to another aspect the flange comprises a diameter or width between 2 and 3 times the diameter of the guiding passageway.

According to another aspect the guiding passageway has a diameter or width approximately between 6 mm and 12 mm.

According to another aspect the first passage opening is located towards an upper portion of the flange.

According to another aspect the first passage opening is located towards an edge of the flange closest to a proximal opening of the gastrointestinal tract of a patient.

According to another aspect the first passage opening is off-centred relative to the flange.

According to another aspect the at least semi-rigid elbow guide is made of medical grade silicone.

According to another aspect the flexible bag is a stoma bag.

According to another aspect the invention broadly comprises a nutrient recycling device for transferring fluid digestive contents from a proximal opening of a gastrointestinal tract to a distal opening of a gastrointestinal tract comprising a feeding catheter as described in any one of the previous clauses.

According to another aspect the invention broadly comprises a nutrient recycling device for transferring fluid digestive contents from a proximal opening of a gastrointestinal tract to a distal opening of the gastrointestinal tract comprising a feeding catheter and elbow guide assembly as described in any one of the previous clauses.

According to another aspect the invention broadly comprises a method of using a feeding catheter to transfer fluid contents from a flexible bag to a distal opening of the gastrointestinal tract comprising:

- providing a feeding catheter as described in any one of the previous clauses;
- stretching the retention feature into its stretched condition for insertion of the feeding catheter through the distal opening of the gastrointestinal tract;
- inserting a first end of the feeding catheter through the distal opening of the gastrointestinal tract into a distal portion of the gastrointestinal tract;
- releasing the retention feature such that it returns to its relaxed condition in the gastrointestinal tract; and
- positioning the flexible bag over the distal opening of the gastrointestinal tract.

According to another aspect the retention feature is stretched using an introducer.

According to another aspect the method of using a feeding catheter further comprising connecting a pump to the second end of the hollow tube before positioning the flexible bag.

According to another aspect the method of using a feeding catheter as described in any of the previous clauses further comprising cutting a portion of the extended diameter portion of the hollow tube before positioning the flexible bag.

According to another aspect the method of using a feeding catheter as described in any one of the previous clauses further comprising positioning an at least semi-rigid elbow guide as described in any one of the previous clauses over the feeding catheter to provide a catheter bend.

According to another aspect the at least semi-rigid elbow guide is positioned such that the at least semi-rigid elbow guide and the feeding catheter have a low-profile in the flexible bag.

According to another aspect the at least semi-rigid elbow guide is positioned such that the feeding catheter is guided downwards such that the second end is located towards a bottom region of the flexible bag.

According to another aspect the method of using a feeding catheter as described in any one of the previous clauses further comprising sliding the at least semi-rigid elbow guide to position the catheter bend along the length of the catheter.

According to another aspect the flexible bag is a stoma bag.

According to another aspect the feeding catheter is adapted for a stoma device, the device transferring fluid digestive contents from a proximal opening to the distal opening of the gastrointestinal tract.

According to another aspect the opening(s) are stomas or fistulas.

Other aspects of the invention may become apparent from the following description which is given by way of example only and with reference to the accompanying drawings.

As used herein the term "fluid", means liquid and/or liquid & solid pulp, mixtures and/or suspensions. In particular, the term "fluid" includes natural chyme (being semi-liquid partially digested food) and/or artificial feeding liquids or pastes etc.

As used herein the term "stoma" is used particularly to denote an opening in the abdomen that is connected to the bowel in order to access the bowel. While typically stomas are surgically created, it is intended that the term is given a wide meaning to include naturally occurring openings such as fistulas etc.

As used herein the term "and/or" means "and" or "or", or both.

As used herein "(s)" following a noun means the plural and/or singular forms of the noun.

The term "comprising" as used in this specification and claims means "consisting at least in part of". When interpreting statements in this specification and claims which include that term, the features, prefaced by that term in each statement, all need to be present but other features can also be present. Related terms such as "comprise" and "comprised" are to be interpreted in the same manner.

BRIEF DESCRIPTION OF THE DRAWINGS

The invention will now be described by way of example only and with reference to the drawings in which:

FIG. 10 shows a schematic view of a nutrient recycling device with the feeding catheter inserted into a distal portion of a gastrointestinal tract.

FIG. 11 shows a schematic view of the nutrient recycling device with a rigid/semi-rigid elbow guide positioned against a patient's abdomen.

FIG. 12 shows a schematic of the nutrient recycling device with a rigid/semi-rigid elbow guide in a different position to FIG. 11.

DETAILED DESCRIPTION OF PREFERRED EMBODIMENTS

According to various configurations as illustrated in FIGS. 1-17, there is provided a feeding catheter 100 and method of using the feeding catheter in a stoma device which will now be described. It will be appreciated that these figures illustrate the general principles of the structure and construction, and that the invention is not limited to the precise configurations illustrated.

The general structure of the various configurations of the present invention as shown in the figures will now be described followed by a description of a method of using the feeding catheter 100.

Figure 1:
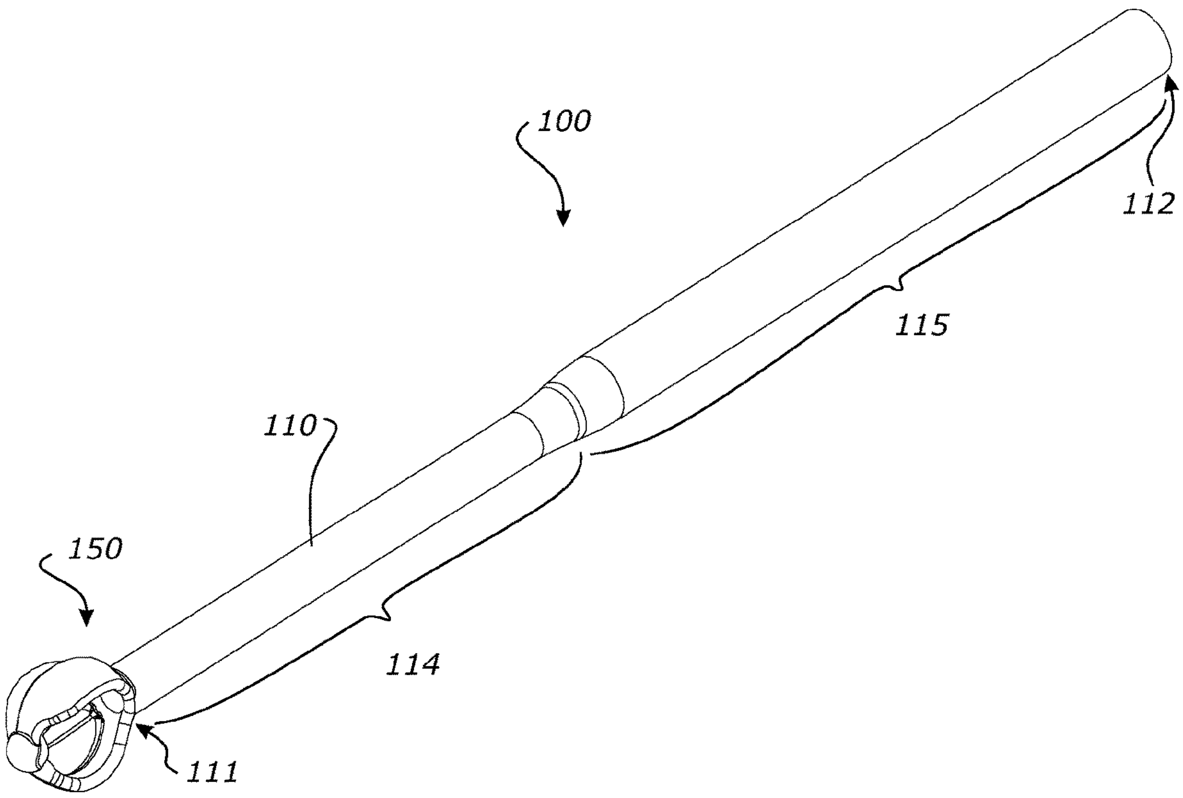
FIG. 1 shows a perspective view of a feeding catheter.
Figure 2:
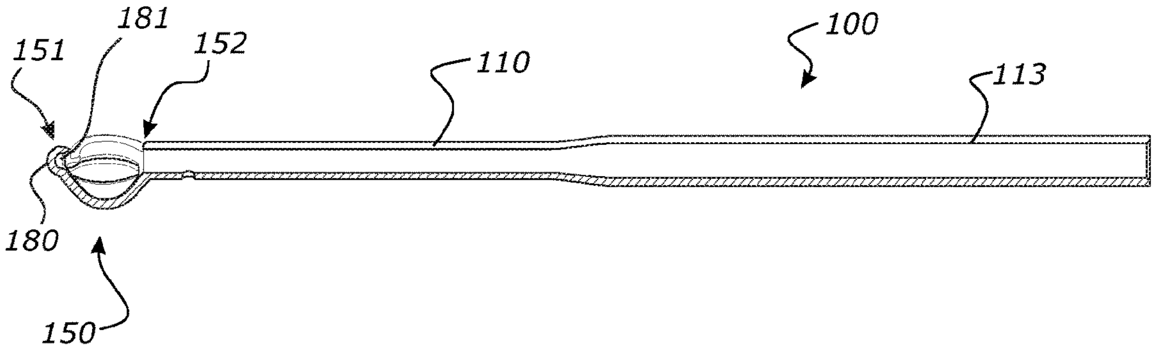
FIG. 2 shows a cross sectional side view of the feeding catheter.

With reference to FIG. 1, in the most preferred configurations, the feeding catheter 100 comprises a hollow tube 110. Preferably the stoma device is a nutrient recycling device 1 and is particularly adapted to be worn externally by a patient.

The hollow tube 110 is an elongate resilient structure which conforms to structures which it is inserted into (e.g. the gastrointestinal tract, in particular the ileum), or contacts against. Preferably, the resilient tube 110 is soft enough to bend and conform. Preferably, it is not rigid and does not remain in a bent shape by itself, but rather elastically returns to a generally elongate shape. In the preferred configurations the feeding catheter 100 is made of a resilient material such as medical-grade silicone. Other catheter materials such known to a person skilled in the art may also be used such as polyurethane, PVC, latex rubber, or other biocompatible plastic elastomers.

The feeding catheter 100 is adapted to be partially inserted into a patient and retained in position for a desired period. The feeding catheter 100 preferably comprises a retention feature 150 (best shown in FIGS. 3 to 6) for retaining the feeding catheter in the distal portion 6 of the gastrointestinal tract once inserted into the patient.

The feeding catheter 100 is adapted to be used in/as part of a stoma device. Preferably, the stoma device is a nutrient recycling device 1 as best shown in FIG. 10.

The feeding catheter 100 feeds the digestive contents 7 from a flexible bag 10 of the nutrient recycling device 1 to the distal opening 4 of the gastrointestinal tract 6.

Preferably fluid and nutrients of the digestive contents 7 are recycled/transferred from the proximal opening 4 to the distal portion 6 of the gastrointestinal tract. Recycling digestive contents 7 can reduce fluid, electrolyte and nutrient losses typically a consequence of ileostomy bypasses. As a result, patients may be less likely to experience dehydration and subsequent renal injury from the ileostomy bypass.

The feeding catheter 100 is adapted to remain in the gastrointestinal tract (preferably ileum) for several days, weeks or months rather than the relatively short duration of a surgery such as with many standard catheters.

In the preferred configurations, the feeding catheter 100 comprises structural features to aid insertion into the patient while also effectively and safely retain the feeding catheter in the patient for the desired period.

The feeding catheter 100 of the present invention is adapted to be inserted into larger cavities (e.g. stoma or fistula orifice) in comparison to standard catheters and has a relatively large tube lumen diameter to allow chyme (including both liquid and semi-solid digestive contents) to pass through and back into the patient.

The nutrient recycling device 1 recycles digestive contents (chyme) 7 from a proximal opening 3 of a gastrointestinal tract to a distal opening 4 of the gastrointestinal tract. The preferred flow pathway of the digestive contents 7 is shown by arrows in FIG. 10.

Preferably, the feeding catheter 100 is introduced into a portion of the ileum (small intestine) of the gastrointestinal tract. This is the region of the gastrointestinal tract involved in ileostomies.

Preferably, the proximal opening 3 and distal opening 4 of a gastrointestinal tract are stomas (or fistulas) on the surface of a patient's abdomen which provides access to the proximal portion 5 of the ileum and distal portion 6 of the ileum respectively.

The nutrient recycling device 1 is adapted to be worn externally by a patient.

It is anticipated the feeding catheter 100 and associated method of using the feeding catheter may be used with other devices to introduce contents (chyme, medicament other contents) to a patient (e.g. via the distal opening 4).

The flexible bag 10 used for the nutrient recycling device 1 may be a typical stoma bag 10. The flexible bag 10 is typically formed from plastic (e.g. polyethylene) and is elastic so that it can lie flat against the wearer's body, while taking the shape of its contents, and expand as necessary such as when digestive contents 7 enter the bag.

The hollow tube 110 of the feeding catheter 100 has a first end 111 adapted to be inserted into a distal portion 6 of the gastrointestinal tract (preferably the ileum) through the distal opening 4 (referenced in FIG. 10). The digestive contents 7 travels from the flexible bag 10 and exits the feeding catheter 100 into the distal portion 7 of the ileum to recycle fluids and nutrients from the proximal portion 5 of the ileum.

The hollow tube 110 of the feeding catheter 100 has a second end 112. Preferably the feeding catheter 100 is soft and flexible so that the second end 112 is located towards the bottom 11 of the flexible bag 10, while maintaining comfort. Preferably, the feeding catheter 100 is kink resistant, such that it can maintain a pathway for the contents 7. Alternatively, the catheter may be a 'lay flat' tube that expands when the pump (described below) operates.

The digestive contents 7 from the flexible bag 10 enters the feeding catheter 100 via the second end 112.

In the preferred configurations, the second end 112 is adapted to be connected to a fluid source, (preferably a pump 9), as shown in FIG. 10.

The pump 9 in the most preferred configurations is located inside or incorporated with the flexible bag 10 (e.g. inside the flexible or incorporated with the bag wall etc.). The digestive content 7 is collected towards the bottom of the flexible bag 10 due to gravity. The pump 9 connected to the second end 111 is adapted to drive the digestive contents

7 up the feeding catheter 100 against gravity. Alternatively, the fluid source is provided by gravity, a syringe or other suitable methods known to a person skilled in the art.

The feeding catheter 100 has a tube lumen 113 between the first end 111 and the second end 112 of the hollow tube 110. The tube lumen 113 is a pathway in the hollow tube 110 which guides and allows fluid communication of the digestive contents 7 from the second end 112 of the hollow tube to the first end 111.

As the feeding catheter 100 is adapted to remain in a patient, the feeding catheter 100 comprises a retaining feature 150, as best shown in FIGS. 3 to 6.

The retention feature 150 has an insertion end 151 and a trailing end 152. The trailing end 152 is preferably located at or towards the first end 111 of the hollow tube.

As previously described, the retaining feature 150 can aid insertion into the patient while also effectively and safely retain the feeding catheter in the patient for the desired period (generally longer than traditional catheters). In the preferred configurations, the retaining feature 150 can be removed safely (does not get stuck) and causes no or limited irritation as it remains in the patient.

In the preferred configurations, the retention feature 150 has a relaxed condition and a stretched condition. The retention feature 150 can be forced from the relaxed condition to the stretched condition. In the stretched condition, the retention feature 150 is shaped for insertion into the distal opening 4 as it has a narrower profile than in the relaxed condition.

Figure 4A:
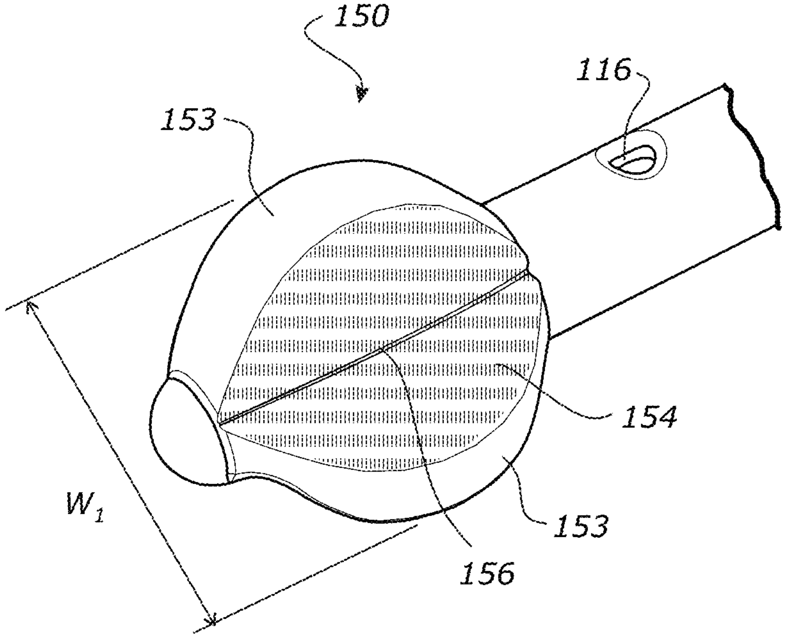
FIG. 4A shows a close-up view of a back side of the retention feature.

Preferably, the maximum width of the retention feature 150 in the stretched condition (width W2 shown in FIGS. 5 and 6) is less than the maximum width of the retention feature in the relaxed condition (width W1 shown in FIG. 4A).

In the stretched condition, the retention feature 150 is preferably stretched in a longitudinal direction such that the width of the retention feature reduces while the length of the retention feature increases.

In the preferred configurations the maximum width of the retention feature 150 in the relaxed condition (width W1) is between 15 mm and 40 mm.

In the preferred configurations the maximum width of the retention feature 150 in the stretched condition (width W2) is between 6 mm and 20 mm.

It is anticipated that the dimensions of the feeding catheter 100 may be adapted to the particular patient or use/situation. The main function of the retention feature 150 is to secure the feeding catheter 100 in the desired position (once inserted) in the distal portion 6 of the gastrointestinal tract for a desired period (several days, weeks or more) without causing excessive discomfort or irritation even as the patient moves.

The retention feature 150 is widest in the relaxed condition when it is at rest (e.g. prior to insertion), or after the force for stretching the retention feature is no longer applied. The ribs 153 are preferably biased to the relaxed condition. For example, the ribs 153 are formed from a resilient material and elastically return to the expanded condition.

Figure 9:
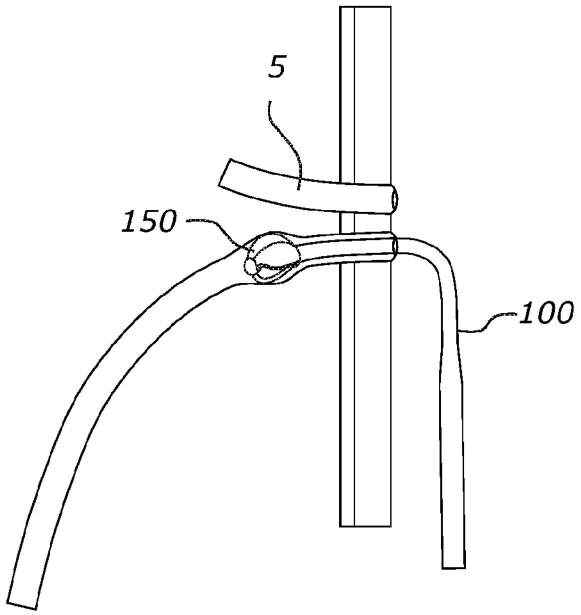
FIG. 9 shows a schematic view of the feeding catheter in the relaxed condition inserted into a distal portion of a gastrointestinal tract.

Preferably, after the feeding catheter 100 has been inserted into the distal portion 6 of the ileum, the ribs 153 naturally expand to its relaxed condition to secure the feeding tube 100 in the distal portion of the gastrointestinal tract (FIG. 9).

The retention feature 150 helps maintain the feeding catheter 100 in position and resists unintentional movement and/or removal of the feeding catheter 100. The retention feature 150 is adapted to secure the feeding tube 100 in the gastrointestinal tract (preferably ileum) for several days, weeks or months. The feeding tube 100 can stay in the ileum for several months (e.g. up to approximately 9 months).

In contrast, some standard catheters are used temporarily for surgeries or other medical procedures and are not designed to be inserted into a patient and retained in position (partially inside and partially exterior the patient) for extended periods.

The retention feature 150 preferably retains the feeding catheter 100 in position (once inserted), even as the patient moves around with daily activities. Movement of the feeding catheter 100 such as the catheter moving further into the patient (potentially damaging the ileum) or coming out from the ileum can be undesirable.

Figure 3:
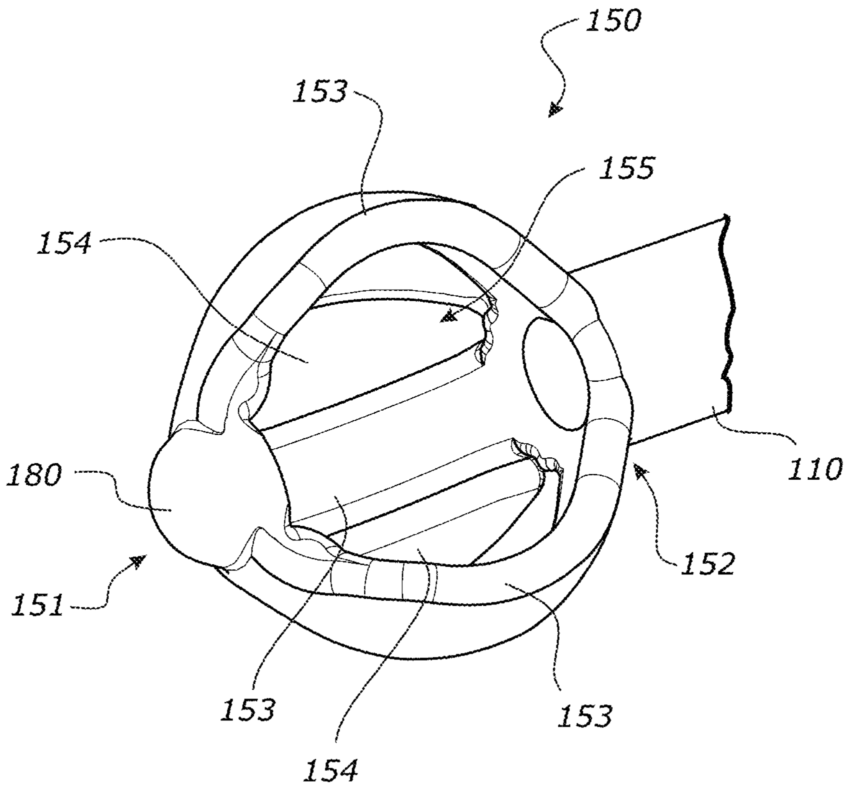
FIG. 3 shows a close-up view of an open side of a retention feature of the feeding catheter.
Figure 4B:
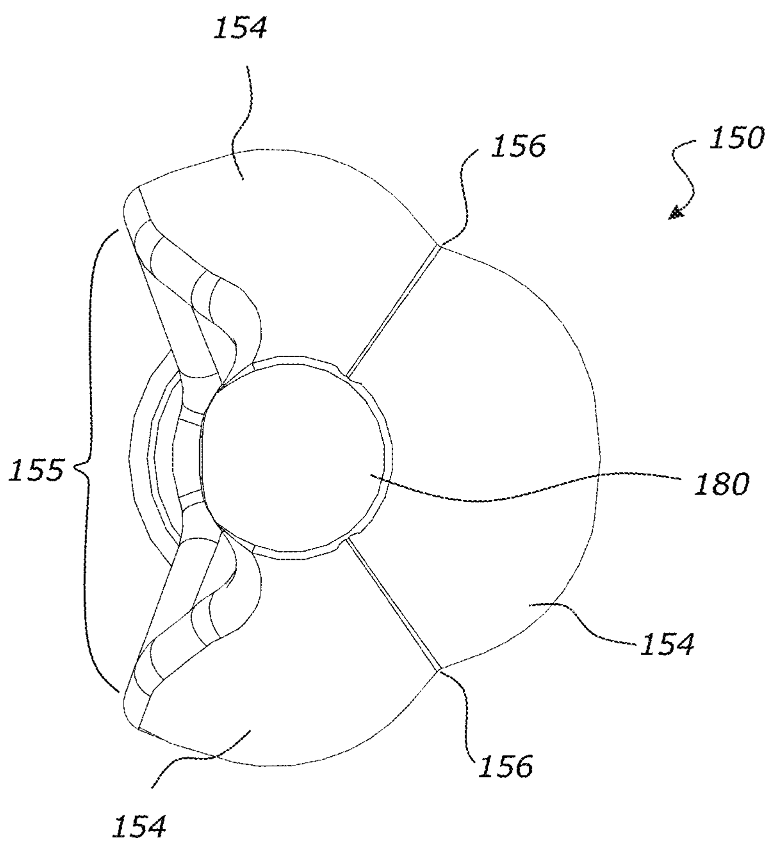
FIG. 4B shows an end up view of the feeding catheter.
Figure 5:
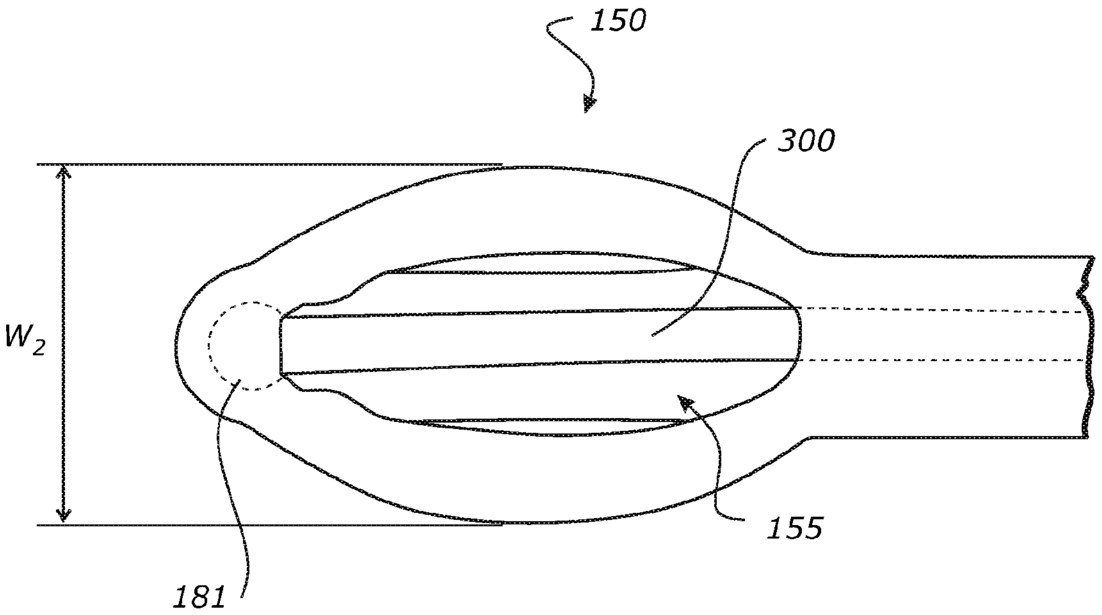
FIG. 5 shows a schematic view of the open side of the retention feature in a stretched condition.

In the most preferred configurations, the retention feature forms a partially open bulbous shape in the relaxed condition as shown in FIGS. 3, 4A and 4B. The resulting shape preferably resembles a catcher's mitt or having a generally hemi-spherical 'cup'.

The retention feature 150 preferably has a plurality of ribs 153 extending outwardly (approximately radially) and longitudinally away from the hollow tube 110 and terminating at a nose junction 180. Preferably, the nose junction 180 is diametrically opposed the first end 111 of the hollow tube 110.

Preferably, the nose 180 of the retention feature aids insertion of the feeding catheter 100 into the distal opening 4 and into the distal portion 6 of the gastrointestinal tract.

The plurality of ribs 153 provides structural integrity to the retention feature 150. The profile and physical characteristics of the ribs 153 allow the retention feature 150 to have sufficient physical integrity (strength/stiffness) to hold its shape (at rest and for retention within a patient.) In the preferred configurations, the ribs 153 have a wall thickness between 1.0 mm and 4.0 mm, while the ribs 153 may be slightly thicker near the nose junction 180 to tailor bending properties along the length of the ribs 153.

Preferably, ribs 153 is formed from a material with appropriate elasticity to allow flex to stretch and allow insertion into the patient, and expand back to its relaxed state after insertion to allow retention in the patient to effectively keep the feeding catheter 100 in position.

The ribs 153 are preferably sufficiently stiff to maintain the shape of the retention feature yet having sufficient elasticity to stretch for insertion.

In the preferred configurations, the retention feature 150 comprises three to five ribs.

In some preferred configurations, the retention feature 150 comprises three ribs.

Preferably, a web wall 154 extends between at least one pair of adjacent ribs 153, as referenced in FIG. 3 and best shown in FIG. 4B. The web wall 154 forms a substantially bulbous (or generally hemi-spherical) shape of the retention feature 150 in the preferred configurations.

Preferably, the retention feature 150 also has an opening 155, that allows digestive contents/chyme to exit the catheter generally sideways (i.e. approximately transverse to the lumen of the catheter, being ±45 degrees of precisely transverse), located between at least one pair of adjacent ribs configured for contents to exit into the gastrointestinal tract from the hollow tube 110. The opening 155 is preferably defined/formed by the pair of adjacent ribs which lack a web wall between the ribs.

Digestive contents 7 (flowing from an outlet of the tube 110) exit through the open side facing opening 155 as shown by the arrows in FIG. 10. Preferably, majority (or all) of the digestive contents 7 from the feeding catheter exit into the lower distal portion of the gastrointestinal tract via the side facing opening 155.

Preferably, the adjacent ribs forming the side facing opening 155 are spaced apart a greater distance than the adjacent ribs joined by web walls 153.

Preferably, the side facing opening 155 opening provides a sufficient exit area for digestive contents to flow out from the feeding catheter 100 into the patient. Though the side facing opening 155 size should be limited so the ribs 153 can maintain the structural integrity of the retention feature 150.

Preferably, the ribs 153 forming the side facing opening 155 has an angular orientation less than 180° apart (viewed from the end of the catheter as shown in FIG. 4B).

In one preferred configuration, the ribs 153 forming the side facing opening 155 has an angular orientation of approximately 140° apart. That is, preferably the ribs 153 are not angularly spaced evenly, but are configured to form a larger side exit 155 so as not to restrict the flow of digestive contents. In some preferred configurations (where the retention feature 150 comprise three ribs), the 'closed' ribs are preferably angularly spaced approximately 110° apart, while the side exit 155 has an angular space of approximately 140°.

Preferably, the side facing opening 155 forms a generally round/circular opening.

Preferably, the retention feature 150 comprises generally hemi-spherical features.

Preferably the shape of the ribs and side facing opening 155 are smooth and rounded without sharp edges, in order to reduce points of pressure which can cause irritation and/or tissue ingrowth. Tissue ingrowth into the catheter is an issue as the feeding catheter 100 can get stuck and require surgery to remove.

In the most preferred configurations, the retention feature 150 comprises a single side facing opening 155. Preferably, the single side facing opening 155 is located between a single pair of adjacent ribs 153. A limited exit, such as through a single side facing opening 155 reduces the possibility of tissue ingrowth. The specific side facing opening 155 works in synergy with the rib and web structure to provide an effective feeding catheter 100 for efficient and safe insertion and retention in the gastrointestinal tract (preferably the small or large intestines). In the preferred configurations, the retaining feature 150 can be removed safely (does not get stuck) and causes no or limited irritation as it remains in the patient.

The feeding catheter 100 is designed to stay inside the gastrointestinal tract which is a unique environment formed from smooth muscle tissue contracting and relaxing involuntary which can make a catheter staying in place difficult.

Further, the feeding catheter 100 is configured to stay in the patient for a desired period (generally longer than traditional catheters). Scaling up an existing catheter would not be suitable in the preferred application for insertion and retention in the gastrointestinal tract and for feeding contents (chyme) back into the patient.

Tissue ingrowth may be possible with standard catheters which are not designed to be left within a patient for extended periods (several days, weeks or months.)

Standard catheters without a suitable retention feature would not be appropriate for insertion into the gastrointestinal tract as the catheter will not stay in place (may be 'swallowed' by the peristalsis movement of the intestines.)

Further, catheters with a structure configured to be inserted and into the gastrointestinal tract with multiple openings would be prone to ingrowth, as adhesions can grow through the openings if there is irritation. If the adhesions grow through and around the catheter, and attach back to the intestine, then the catheter can become stuck causing tears and/or require surgery for removal.

Optionally, the feeding catheter 100 has an aperture 116 on the hollow tube 110 towards the first end 111 of the tube, referenced in FIG. 4A. The aperture 116 is preferably a suction break/relief to prevent the tube from sucking onto the bowel wall in situations where the pump stops pumping and chyme flows back into the bag.

Preferably, the aperture 116 is located a sufficient distance away from the side facing opening 155 such that that if any adhesions occur due to irritation, then there is a low chance that they could grow through the tube and out the other side, making the tube stuck in place.

Preferably, the ribs 153 are more rigid than the web wall 154. The web wall 154 is best shown in FIG. 4A as the dotted outer wall region of the retention feature 150.

Preferably, the web wall 154 is highly flexible relative to the ribs 153. The web wall 154 is preferably formed from a thin flexible film or membrane. The thin web wall 154 between the ribs 153 form a wall to direct chyme to the side facing opening 155 and prevent ingrowth into the regions between the ribs.

In the preferred configurations, the web wall 154 collapses as the width/diameter of the retention feature 150 reduces for insertion into the gastrointestinal tract of the patient (i.e. as the ribs deform into the stretched condition).

In the preferred configurations, the web wall 154 is configured to collapse generally inwardly in the stretched condition. The web wall 154 collapses generally inwards in a direction towards a central longitudinal axis of the feeding catheter 100.

The highly flexible thin web wall 154 (relatively thinner and more flexible than the ribs) allows it to collapse in a low profile, between adjacent ribs 153.

Preferably, the thin web wall 154 collapses between the ribs 153 in the stretched condition, such that the walls are folded and approximately aligned with the ribs. In this configuration, preferably the web walls 154 do not collapse into the lumen space of the catheter to block flow or unduly limit flow.

Figure 6:
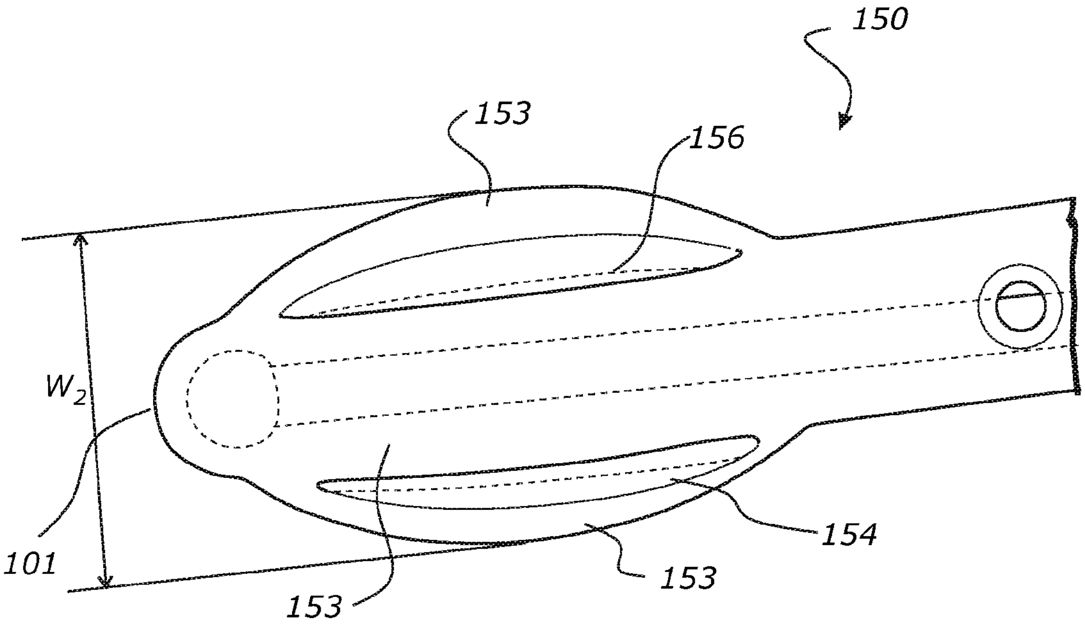
FIG. 6 shows a schematic view of the back side of the retention feature in a stretched condition.

In some configurations, the web wall 154 comprises a score-line 156 such that the web wall is configured to collapse in the stretched condition (referenced in FIG. 4A and FIG. 6). The web wall 154 folds inwards along the score-line, and the plurality of ribs 153 move together such that the retention feature 150 takes its narrower stretched form for insertion.

In some configurations, the score-line 156 is a longitudinal indent or crease along the web wall 157.

Preferably, the web wall 154 has a wall thickness less than a wall thickness of the plurality of ribs 153.

In the preferred configurations, the web wall 154 has a wall thickness less than 50% the wall thickness of the ribs 153.

More preferably, the web wall 154 has a wall thickness less than 30% the wall thickness of the ribs 153.

More preferably, the web wall 154 has a wall thickness less than 20% the wall thickness of the ribs 153.

In the most preferred configurations, the web wall 154 has a wall thickness between 10% and 20% of the wall thickness of the ribs 153.

In the preferred configurations, the web wall 154 has a wall thickness between 0.2 mm and 0.8 mm.

In the preferred configurations, the ribs 153 have a wall thickness between 1.0 mm and 4.0 mm.

Figure 7:
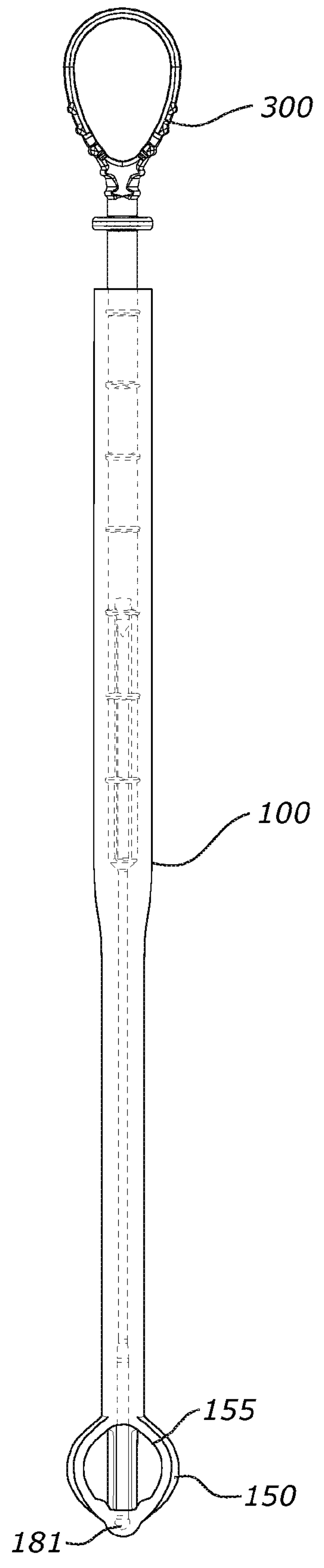
FIG. 7 shows a side view of the feeding catheter and an introducer.
Figure 8:
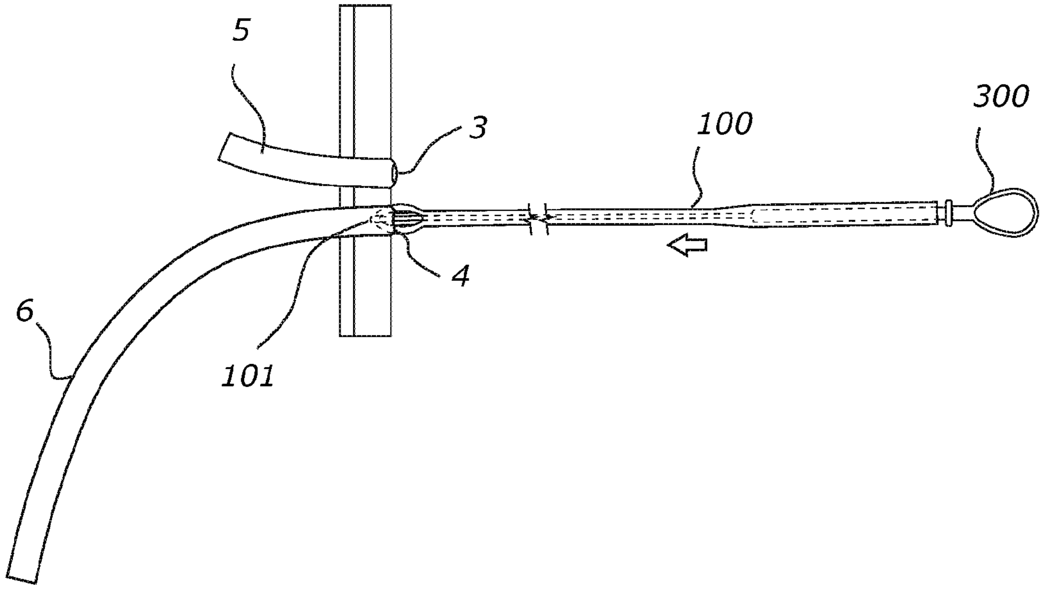
FIG. 8 shows a schematic view of the feeding catheter in the stretched condition partially inserted into a distal portion of a gastrointestinal tract.

In the preferred configurations, to move the feeding catheter 100 from the relaxed condition to the stretched condition, an introducer 300 can be used, as shown in FIGS. 7 and 8.

Preferably, the tube lumen 113 is configured to receive an introducer 300. The introducer is preferably an introducer rod or a similar instrument known to a person skilled in the art.

In these configurations, preferably, the introducer 300 is configured to engage with an internal surface of the nose junction 180 to force the retention member from the relaxed condition to the stretched condition. The tip of the introducer 300 presses internally against the internal surface of the nose junction 180 in an insertion direction, while the tube 100 is held in position or pulled in the opposite direction. As the retention member 150 is forced into the stretched condition, preferably the width/diameter of the member reduces and length of the member increases for insertion.

In some configurations, the retention feature 150 further comprises a pocket 181 on the inner surface of the nose junction to receive a tip of the introducer. The pocket is an indent on the inner surface of the nose shaped and configured to receive and keep the tip in position during stretching.

In the preferred configurations, the hollow tube 110 has a neck portion 114 located towards the first end 111 of the tube. Preferably, the hollow tube 110 also has an extended diameter portion 115 located towards the second end 112. The extended diameter portion 115 has a tube diameter greater than the neck portion 114.

The extended diameter portion 115 has a greater diameter than the neck portion 114 as it is adapted to be inside the flexible bag 10 and connected to a pump 9. The neck portion 114 has a smaller diameter so it can be inserted into the gastrointestinal tract 2 with minimal discomfort.

Preferably, the extended diameter portion 115 is a substantial portion of the hollow tube 110, so that the hollow tube 100 can be cut at various positions along the extended diameter portion 115 so that it is a suitable length for the second end 112 of the tube to be positioned towards the bottom of the flexible bag 10. The second end 112 of the tube (and therefore the pump 9) should be positioned towards the bottom, as the digestive content 7 is collected towards the bottom of the flexible bag 10 due to gravity.

As previously described, in the preferred configurations, a pump 9 is connected to the second end 112 of the tube 110 to drive the digestive contents 7 up the feeding catheter 100 against gravity and into the distal portion 6 of the ileum.

Preferably, the feeding catheter 100 length is also customised to the patient to minimise discomfort, and that the catheter does not bulge outwards against the flexible bag 10 due to excess tube length.

Preferably, the extended diameter portion 115 makes up enough of the hollow tube 110 to allow cutting of the hollow tube 100 for customisation of the feeding catheter 100 length to accommodate a variety of patient anatomies and flexible bags 10. As the anatomy of patients varies, is should be appreciated that it would be advantageous if the feeding catheter 100 could be cut to be customised in length accordingly, leaving a portion of the extended diameter portion 115 to be connected to the pump 9.

Some traditional catheters do not have an extended diameter portion and would not be suitable to connect to a pump 9. Other traditional catheters have a portion which has an extended diameter portion, however these portions are usually short and would not provide enough length to be cut and customised to the patient/stoma bag as described above.

It may also be useful to cut and customisable the hollow tube 110 length so that the feeding catheter 100 has a flat-profile in the flexible bag 10. If the feeding catheter 100 is too long it can bulge outwards against the flexible bag 10. It should be appreciated that patients would typically desire a discreet stoma bag 10 with a flat-profile.

Furthermore, a customised catheter length may be advantageous as it can increase comfort and/or reduce the likelihood of damage to the gastrointestinal tract (e.g. pressure necrosis) due to external pressure exerted and transferred to the gastrointestinal tract, by movement of the feeding catheter.

Preferably, the extended diameter portion 115 comprises an external diameter approximately between 10 mm and 20 mm.

Most preferably, the extended diameter portion 115 comprises an external diameter approximately between 10 mm and 15 mm.

In one configuration the diameter of the extended diameter portion 115 is approximately 12.5 mm.

Preferably, the neck portion 114 comprises an external diameter approximately between 4 mm and 12 mm.

Most preferably, the neck portion 114 comprises an external diameter approximately between 8 mm and 10 mm.

In one configuration the diameter of the neck portion 114 is approximately 9.3 mm.

Preferably, the extended diameter portion 115 comprises a length at least 25% of the feeding catheter 100 length.

Most preferably, the extended diameter portion 115 comprises a length at least 40% of the feeding catheter 100 length.

In some configurations, the extended diameter portion 115 is at least 100 mm long of a feeding catheter having a length of approximately 300 mm.

Preferably, the feeding catheter 100 is preferably comprises a resilient material so that it can safely (and with limited discomfort to the patient) conform to structures which it is inserted into, or contacts against.

In the preferred configurations the feeding catheter 100 is formed from silicone (medical-grade). Other catheter materials such known to a person skilled in the art may also be used such as polyurethane, PVC, latex rubber, or other biocompatible plastic elastomers.

Preferably, the feeding catheter 100 is an integrated component. The hollow tube 110, the retention feature 150, are formed as one component.

The feeding catheter 100 is moulded as one component, or can be formed with other techniques know to a person skilled in the art.

In some independent configurations, an at least semi-rigid elbow guide 200 is adapted to receive and guide the feeding catheter 100 in the flexible bag 10 as shown in FIG. 10. The rigid/semi-rigid elbow guide 200 is most preferably used with the feeding catheter 100 described above. However, it is anticipated that in some independent configurations, the rigid/semi-rigid elbow guide 200 may be used with other catheters.

Preferably, the rigid/semi-rigid elbow guide 200 is part of a nutrient recycling device 1 for recycling digestive contents from a proximal opening 5 of a gastrointestinal tract to a distal opening 6 of the gastrointestinal tract, as described above.

The rigid/semi-rigid elbow guide 200, has a bend adapted to guide the feeding catheter 100 so that the catheter forms and maintains a catheter bend 120 in a suitable location. As best shown in FIG. 10, preferably, the feeding catheter 100 is maintained in a bent shape (by at least semi-rigid elbow guide 200) so the retention feature 150 and the neck portion 114 is positioned in the distal portion 6 of the gastrointestinal tract, while extended diameter portion 115 is substantially perpendicular (to the extended diameter portion 114) and pointing downwards so the second end 112 (of the hollow tube 110) is located towards the bottom region 11 of the flexible bag 10.

The rigid/semi-rigid elbow guide 200 is formed from an at least semi-rigid material which is able to maintain the desired shape (provide a bend) of the feed catheter 100.

Without the rigid/semi-rigid elbow guide 200, the feeding catheter 100 may press against the flexible bag 10, as it naturally protrudes or projects laterally from the distal opening 4. This may be undesirable, as the feeding catheter 100 would bulge against the flexible bag 10 and would be less discreet.

Figure 13:
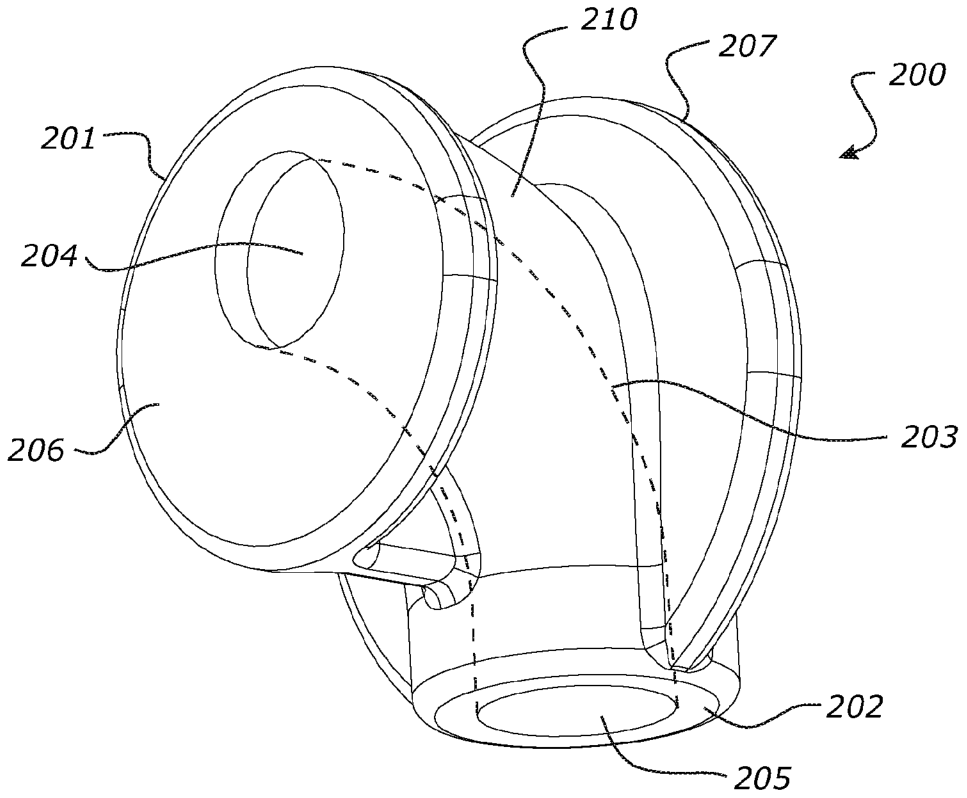
FIG. 13 shows a perspective view of an elbow guide.
Figure 14:
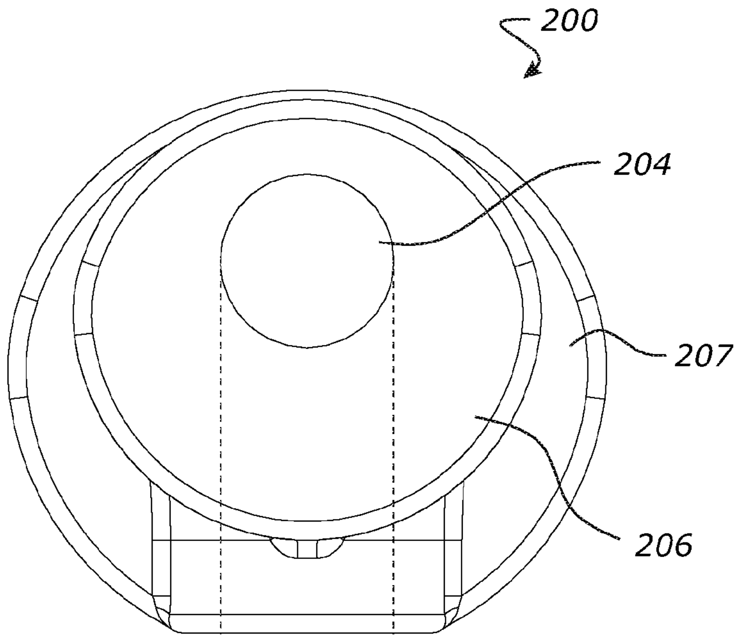
FIG. 14 shows a front view of the elbow guide of FIG. 13.

In the most preferred configurations, the rigid/semi-rigid elbow guide 200 is slidably moveable relative to the feeding catheter 100 to adjust the catheter bend 120 position (as shown in FIGS. 13 and 14). The catheter bend 120 position may be adjusted to customise the catheter profile to different patients/stoma bags or adjusted for comfort at different times for the same patient.

Preferably, the profile of the rigid/semi-rigid elbow guide 200 reduces the likelihood of the feeding catheter 100 from kinking (folding of the tubular, such that the pathway/flow of the contents is blocked). Preferably, the radius of the bend of the rigid/semi-rigid elbow guide 200 is sufficient to prevent kinking.

In the preferred configurations, the rigid/semi-rigid elbow guide 200 slidably moves relative to the feeding catheter 100 by stretching the length of the catheter to decrease the diameter of the catheter. As the rigid/semi-rigid elbow guide 200 has a guiding passage 203 diameter greater than the catheter 100 in this condition, the guide is able to slide along the length of the catheter.

Figure 15:
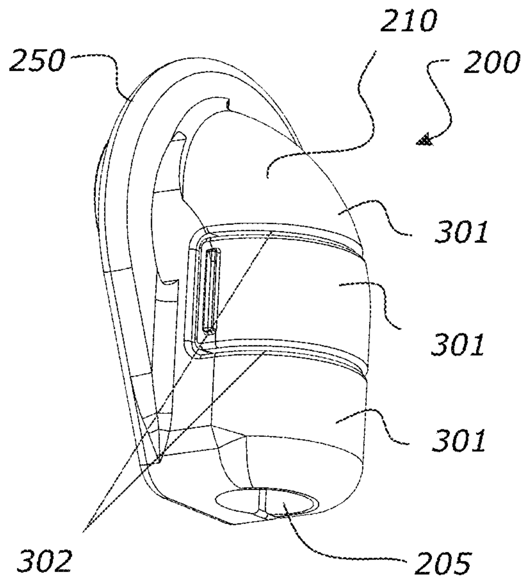
FIG. 15 shows a perspective view of another elbow guide.
Figure 16:
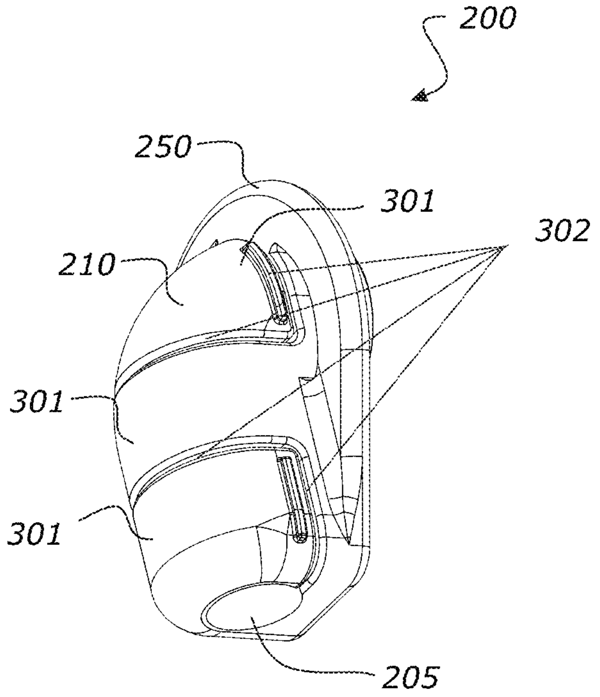
FIG. 16 shows another perspective view of the elbow guide of FIG. 15.
Figure 17:
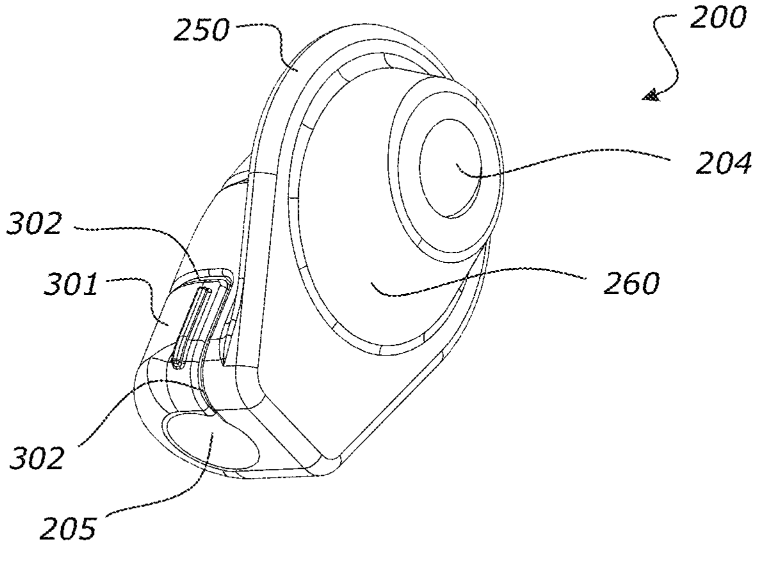
FIG. 17 shows another perspective view of the elbow guide of FIG. 15.

With reference to FIGS. 15 to 17, an elbow guide 200, with alternative grip features is shown, and will now be described in more detail. It will be appreciated that many features are shared with the guide 200 shown in FIGS. 13 & 14, and therefore use the same reference numbers.

The guide body 210 in this configuration comprises a plurality of cantilevered fingers 301 (separated from the rest of body 210, by cuts 302) in order to provide additional resilience to the semi-rigid body. As shown the cantilevered fingers 301 generally encompass the feeding catheter inner passageway (203—not shown), and act to resiliently grip a feeding catheter within. In this configuration, the material of the body 210 may be comparatively more rigid (than the previous configuration) and the cantilevered fingers provide the required semi-rigid structure that interacts with the catheter.

In the illustrated configuration, there are at 3 cantilevered fingers 301, arranged to alternately interleave one another, although it is anticipated that more than 3 cantilevered fingers 301 may be provided.

In the configuration of FIG. 15, a single flange 250 is provided, on body 210. Flange 250 preferably tapers towards the lower end of body 210 (near aperture 205), in order that the outer periphery of the elbow takes on a tapered shape, aiding with insertion into a stoma bag.

In the configuration of FIG. 15, there is also a tapered transition 260 between the aperture 204 that is adjacent a stoma (in use), towards the flange 250. This transition 260, provides a cone to engage with a stoma, and thereby may further assist to retain the assembly imposition (when in use).

Preferably, the diameter of the guiding passage 203 has the same or similar diameter as the feeding catheter 100 in a non-stretched condition to keep the rigid/semi-rigid elbow guide 200 at the desired location on the catheter.

Preferably, the rigid/semi-rigid elbow guide 200 has a low-profile. The rigid/semi-rigid elbow guide 200 positions the catheter bend 120 such that the feeding catheter 100 does not bulge too far outwards against the flexible bag 10. Preferably wearing a stoma bag 10 with the feeding catheter 100 is not significantly more burdensome than wearing a traditional stoma bag without internal components.

The rigid/semi-rigid elbow guide 200 also preferably positions the catheter bend 120, so that the elbow bend guides the feeding catheter 100 downwards and the second end 202 is located towards the bottom region 11 of the flexible bag 10.

In some configurations the rigid/semi-rigid elbow guide 200 is formed from silicone. It is anticipated, other materials with similar rigid/semi-rigid properties can be used to form the rigid/semi-rigid elbow guide 200.

The semi-rigid elbow guide 200 in the preferred configurations is moulded in the bent configuration (to form the catheter bend 120), so when the feeding catheter 100 is inserted into the guide, the guide bends it.

In the preferred configurations, the material of the semi-rigid elbow guide 200 is the same (or very similar) physical properties as the feeding catheter 100. However, it has a different cross-sectional area in the axis of bending, which give it more resistance to bending (in comparison to the feeding catheter).

In other configurations, the semi-rigid elbow guide 200 is made from a material with different properties to the feeding catheter 100, resulting in a more rigid guide to form the catheter bend.

In the preferred configurations, the rigid/semi-rigid elbow guide 200 has a guide body 210 having a first end 201 and a second end 202 as referenced in FIG. 13.

Preferably, the rigid/semi-rigid elbow guide 200 has a guiding passageway 203 extending between the first end 201 and second end 202 for the feeding catheter 100 to pass through and guiding the catheter bend 120. The guiding passageway 203 has a first passage opening 204 and a second passage opening 205.

Preferably, the rigid/semi-rigid elbow guide 200 has a flange 206 at the first end 201 of the guide body 210. The flange 206 provides a substantially flat surface adapted to engage an inner surface of the flexible bag 10. The flange 206 can help position the rigid/semi-rigid elbow guide in the flexible bag 10, which in turn positions the feeding catheter 100.

Peristalsis of the bowel can grasp an object like the retention feature 150 and pull it downstream, which is undesirable. In the preferred configurations, the flange 206 is adapted to engage with an exterior surface of the patient's body to maintain the position of the feeding catheter. The flange 206 preferably prevents the feeding catheter 100 from being pulled down into the stoma (distal opening) 4, or the feeding catheter 100 from being pulled into or "swallowed" into the stoma, if the second end 112 of the feeding catheter 100 is free (e.g. not connected to the pump 9).

Preferably, the first passage opening 204 is located towards an edge of the flange, such that there is a substantial engaging surface area is located away from the edge to engage with an exterior surface of the patient's body to maintain the position of the feeding catheter.

The first passage opening 204 located towards an edge of the flange allows digestive contents/chyme 7 to flow out of the proximal opening 3 (i.e. the flange does not cover the proximal opening but has support against the flexible bag 10 and the body of the patient). Typically, proximal and distal stomas 3, 4 are located close together on an outer surface a patient's body. If the first passage opening 204 of the flange 206 was located towards the centre of the flange, the flange may cover or partially cover the proximal opening 3, which is undesirable.

Preferably, the first passage opening 204 is located towards an edge of the flange closest to a proximal opening of the gastrointestinal tract of a patient.

In the preferred configurations, the flange 206 is off-centre relative to the first passage opening 204 of the rigid/semi-rigid elbow guide 200 as best shown on FIG. 8.

In some preferred configurations, the first passage opening 204 is off-centred relative to the flange 206.

Preferably, the first passage opening 204 is located towards an upper portion of the flange 204.

Preferably, the flange 206 has a diameter (if the flange is circular) or length (if the flange is not-circular) between 2 and 3 times the diameter of the guiding passageway 203. Preferably, the guiding passageway 203 has a diameter approximately between 6 mm and 12 mm.

Most preferably, the guiding passageway 203 has a diameter approximately between 8 mm and 10 mm.

In some configurations, the flange 206 has a circular cross-section as illustrated. It is anticipated the flange 206 can take the form of another shape e.g. rectangular.

In some configurations, the rigid/semi-rigid elbow guide 200 comprises a supplementary flange 207 (not present in the configurations of FIGS. 15 to 17).

Preferably, the secondary flange 207 spaced from the (primary) flange 206.

Preferably, the secondary flange 207 comprises a diameter/width greater than the flange 206.

Preferably, the secondary flange 207 acts as a 'back up' flange if the primary flange 206 does not stop the elbow guide 200 migrating into the stoma. The primary flange 206 is sized to not block the proximal stoma, allowing chyme to come out. Ideally the front primary flange 206 would be large to stop the feeding catheter from migrating into the stoma. However, if the smaller flange 206 does gets sucked into the intestine, the larger secondary flange 207 preferably engage with an exterior surface of the patient's body to maintain the position of the feeding catheter.

Following the description of the structure of the present invention described above, a general description of the method of using the feeding catheter 100 will now be described. The feeding catheter 100 is used to feed recycled digestive nutrients 7 from a flexible bag 10 to a distal opening 4 of the gastrointestinal tract 6. The flexible bag 10 may be a typical stoma bag and is preferably formed from plastic (eg polyethylene). The flexible bag 10 is easily deformed so that it can lie flat against the patient's abdomen and also expand as necessary when digestive contents enters it.

Preferably the digestive contents flow from a proximal portion 5 of the gastrointestinal tract, through a proximal opening 3 of the gastrointestinal tract and are collected towards the bottom region 11 of the flexible bag 10 (of the nutrient recycling device 1) by gravity. Preferably the gastrointestinal tract is the ileum (small intestine) and preferably the gastrointestinal tract openings are stomas (created by an ileostomy procedure) or fistulas on the surface of a patient's abdomen.

Firstly, a feeding catheter 100 as described above is provided. A first catheter end 101 (insertion end) of the feeding catheter 100 is preferably inserted through the distal opening 4 of the gastrointestinal tract 2 and into a distal portion 6 of the gastrointestinal tract 2.

Preferably, the retention feature 150 is stretched into its stretched condition for insertion of the feeding catheter 100 through the distal opening 4 of the gastrointestinal tract.

Preferably, the retention feature 150 is stretched using an introducer 300.

Once in the stretched condition, preferably a first end of the catheter is inserted through the distal opening 4 of the gastrointestinal tract into a distal portion of the gastrointestinal tract.

Once the feeding catheter 100 is at least partially inserted, the retention feature 150 is released such that it returns to its relaxed condition in the gastrointestinal tract, so that the ribs 153 and the web wall 154 of the retention feature 150 elastically expand and return to the relaxed condition. Therefore, the feeding catheter 100 is secured by the retention feature 150 in position in the distal portion 6 of the gastrointestinal tract.

In the preferred configurations, the flexible bag 10 is positioned over the proximal and distal openings 3, 4 of the gastrointestinal tract 2 after the feeding catheter has been inserted.

In some configurations, a portion of the extended diameter portion 115 of the hollow tube 110 is cut before positioning the flexible bag to customise the tube length to the patient/stoma bag position.

In the preferred configurations, a pump 9 is connected to the second end 112 of the hollow tube 110 before positioning the flexible bag 10.

Preferably, the feeding catheter 100 has a low-profile in the flexible bag 10. Preferably, the feeding catheter 100 is positioned such that the second end 112 of the hollow tube 110 is located towards a bottom region 11 of the flexible bag 10.

In some preferred configurations, a rigid/semi-rigid elbow guide 200 is provided and positioned over the feeding catheter 100 to provide a catheter bend 120.

Preferably, the rigid/semi-rigid elbow guide 200 can slide relative to the feeding catheter to position the catheter bend 120 at a suitable position.

Preferably, the rigid/semi-rigid elbow guide 200 is positioned such that the rigid/semi-rigid elbow guide and the feeding catheter 100 have a low-profile in the flexible bag 10 (i.e. the feeding catheter does not bulge too far outwards against the bag).

Preferably, the rigid/semi-rigid elbow guide 200 is positioned such that the feeding catheter 100 is guided downwards such that the second end 112 is located towards a bottom region 11 of the flexible bag 10.

In some configurations, the rigid/semi-rigid elbow guide 200 is positioned to set the depth of insertion of the feeding catheter into the patient.

It will be appreciated that the foregoing provides an improved feeding catheter that is resilient (cannot over expand, can withstand degradation for up to a month in a patient's body and be kink resistant) but is soft enough to conform to structures it is inserted into or contacts against.

Similarly, the improved feeding catheter is also soft enough to be cut: so the second end of the feeding catheter can be positioned towards the bottom of the flexible bag, to be customised to suit patient anatomy/stoma bag type, to minimise discomfort, to prevent the feeding catheter bulging outwards against the flexible bag, and to prevent the feeding catheter pressing downwards on the flexible bag causing pressure necrosis/damage to the gastrointestinal tract.

Further, the improved feeding catheter is smooth and without sharp edges in order to reduce discomfort, prevent an ulcer perforating the intestine, and reduce pressure causing irritation, adhesions and/or granulation that may cause tissue ingrowth that may cause the feeding catheter to get stuck requiring surgery to be removed.

The forgoing provides an at least semi rigid elbow guide (that can be slidably moved and is kink resistant) to position the feeding catheter in a bent shape to prevent bulging outwards against the flexible bag and guide the second end of the feeding catheter downwards towards the bottom region of the flexible bag.

Further, a flange on the at least semi-rigid elbow guide is adapted to support the flexible bag against the patient's abdomen, (and may optionally position the at least semi-rigid elbow guide against an inner surface of the flexible bag), and prevent the feeding catheter from being pulled into the distal portion of the gastrointestinal tract.

To those skilled in the art to which the invention relates, many changes in construction and widely differing embodiments and applications of the invention will suggest themselves without departing from the scope of the invention as defined in the appended claims.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

The invention claimed is:

1. A feeding catheter adapted to transfer fluid into an opening of a gastrointestinal tract, the feeding catheter comprising:
- a hollow tube having:
  - a first end adapted to be inserted into a distal portion of the gastrointestinal tract through a distal opening;
  - a second end adapted to be connected to a fluid source; and
  - a tube lumen between the first end and the second end of the hollow tube defining a fluid pathway;
- a retention feature adapted to retain at least a portion of the feeding catheter in the distal portion of the gastrointestinal tract, the retention feature located at or towards the first end of the hollow tube and comprises:
  - an insertion end and a trailing end, the trailing end located at or towards the first end of the hollow tube;
  - at least 3 ribs extending outwardly and longitudinally away from the hollow tube and terminating at a nose junction;
  - a flexible membrane web wall extending completely between all but one pair of adjacent ribs to define a single side facing opening located between the one pair of adjacent ribs configured for fluid to exit into the gastrointestinal tract; and
- wherein the retention feature comprises a relaxed condition and a stretched condition for insertion through the distal opening; and
- wherein a maximum width of the retention feature in the stretched condition is less than a maximum width of the retention feature in the relaxed condition, and
- wherein the retention feature forms a partially open bulbous shape in the relaxed condition.

2. The feeding catheter as claimed in claim 1, wherein the pair of adjacent ribs forming the side facing opening lacks a web wall between the pair of adjacent ribs.

3. The feeding catheter as claimed in claim 1, wherein the pair of adjacent ribs forming the side facing opening are spaced apart a greater distance than the adjacent ribs joined by web walls.

4. The feeding catheter as claimed in claim 1, wherein the ribs forming the side facing opening have:

a) an angular orientation less than 180° apart, or b) an angular orientation of 140° apart.

5. The feeding catheter as claimed in claim 1, wherein the web wall has a wall thickness:

a) less than a wall thickness of the plurality of ribs, or b) less than 20% the wall thickness of the ribs, or c) 10% to 20% of the wall thickness of the ribs.

6. The feeding catheter as claimed in claim 1, wherein the tube lumen is configured to receive an introducer, and wherein the introducer is configured to engage with an internal surface of the nose junction to force the retention feature from the relaxed condition to the stretched condition.

7. The feeding catheter as claimed in claim 1, further comprising an aperture on the hollow tube towards the first end of the tube to provide a suction break.

8. The feeding catheter as claimed in claim 1, wherein the retention feature comprises three to five ribs.

9. The feeding catheter as claimed in claim 1, wherein the hollow tube comprises:

a neck portion located towards the first end; and an extended diameter portion located towards the second end, and wherein the extended diameter portion has a tube diameter greater than the neck portion.

10. The feeding catheter as claimed in claim 9, wherein:

a) the extended diameter portion comprises an external diameter between 10 mm and 20 mm, or b) the extended diameter portion comprises an external diameter between 10 mm and 15 mm, or c) the neck portion comprises an external diameter between 4 mm and 12 mm, or d) the neck portion comprises an external diameter between 8 mm and 10 mm.

11. A feeding catheter and elbow guide assembly comprising:

the feeding catheter as claimed in claim 1;

an at least semi-rigid elbow guide for receiving and guiding the feeding catheter in a flexible bag, the at least semi-rigid elbow guide comprising:

a guide body having a first end and a second end, and a guiding passageway extending between the first end and second end for the feeding catheter to pass through, the guiding passageway having a bend for maintaining the catheter in a bent position and the guiding passageway having a first passage opening and a second passage opening; and a flange at the first end of the guide body to engage with an exterior surface of the patient's body adapted to maintain the position of the feeding catheter; and wherein the first passage opening is located towards an edge of the flange such that there is a substantial engaging surface area located away from the edge to engage with the exterior surface of the patient's body; and wherein the at least semi-rigid elbow guide is positioned over the feeding catheter to maintain the catheter in the bent position.

12. The feeding catheter and elbow guide assembly as claimed in claim 11, wherein the guide body comprises a plurality of cantilevered fingers generally encompassing the guiding passageway and configured to resiliently grip a feeding catheter.

13. A nutrient recycling device for transferring fluid digestive contents from a proximal opening of a gastrointestinal tract to a distal opening of a gastrointestinal tract comprising: the feeding catheter of claim 1.

14. A method of using a feeding catheter to transfer fluid contents from a flexible bag to a distal opening of the gastrointestinal tract comprising:

providing the feeding catheter as claimed in claim 1;

stretching the retention feature into its stretched condition for insertion of the feeding catheter through the distal opening of the gastrointestinal tract;

inserting the first end of the feeding catheter through the distal opening of the gastrointestinal tract into a distal portion of the gastrointestinal tract;

releasing the retention feature such that it returns to its relaxed condition in the gastrointestinal tract; and positioning the flexible bag over the distal opening of the gastrointestinal tract.

15. The method of using a feeding catheter as claimed in claim 14, wherein the retention feature is stretched using an introducer.

16. The method of using a feeding catheter as claimed in claim 14, further comprising connecting a pump to the second end of the hollow tube before positioning the flexible bag.

17. The method of using a feeding catheter as claimed in claim 14, further comprising cutting a portion having an extended diameter of the hollow tube before positioning the flexible bag.

18. The method of using a feeding catheter as claimed in claim 14, further comprising positioning an at least semi-rigid elbow guide over the feeding catheter to provide a catheter bend.

19. The method of using a feeding catheter as claimed in claim 18, wherein the at least semi-rigid elbow guide is positioned such that the feeding catheter is guided downwards such that the second end is located towards a bottom region of the flexible bag.

20. The method of using a feeding catheter as claimed in claim 18, further comprising sliding the at least semi-rigid elbow guide to position the catheter bend along the length of the catheter.

* * * * *